(12) United States Patent
Roberts et al.

(10) Patent No.: US 6,951,880 B2
(45) Date of Patent: Oct. 4, 2005

(54) ARYL AND HETEROARYL COMPOUNDS AS ANTIBACTERIAL AND ANTIFUNGAL AGENTS

(75) Inventors: Christoher Don Roberts, Belmont, CA (US); Jesse Daniel Keicher, Menlo Park, CA (US); Mikail Hakan Gezginci, Foster City, CA (US); Mark Douglas Velligan, Montara, CA (US)

(73) Assignee: Genelabs Technologies, Inc., Redwood City, CA (US)

(*) Notice: Subject to any disclaimer, the term of this patent is extended or adjusted under 35 U.S.C. 154(b) by 0 days.

(21) Appl. No.: 10/438,377

(22) Filed: May 15, 2003

(65) Prior Publication Data

US 2003/0220340 A1 Nov. 27, 2003

Related U.S. Application Data

(60) Provisional application No. 60/381,941, filed on May 16, 2002.

(51) Int. Cl.⁷ ................... A61K 31/403; C07D 209/56; C07D 209/93; A61P 31/00
(52) U.S. Cl. .................. 514/411; 514/454; 514/352.13; 544/366; 544/367; 548/427; 549/458
(58) Field of Search ........................ 548/427; 549/458; 544/366, 367; 514/411, 454, 252.13

(56) References Cited

U.S. PATENT DOCUMENTS

| | | | |
|---|---|---|---|
| 5,760,069 A | * | 6/1998 | Lukas-Laskey et al. .... 514/411 |
| 6,294,565 B1 | | 9/2001 | Dykstra et al. |
| 6,326,395 B1 | | 12/2001 | Tidwell et al. |
| 6,635,668 B1 | | 10/2003 | Tidwell et al. |
| 2002/0019437 A1 | | 2/2002 | Boykin et al. |

OTHER PUBLICATIONS

Takiguchi et al., 1988, CAS: 108:213874.*
Assy et al., 1995, CAS: 124:176041.*
Akalayeva et al., 1995, CAS:123:251041.*
Bally, Christian, et al., Sequence–Specific DNA Minor Groove Binders, Design and Synthesis of Netropsin and Distamycin Analogues, *Bioconjugate Chemistry*, vol. 9, No. 5, (Sep./Oct. 1998), pp. 513–538.
Fillpowsky, Mark E., et al., Linked Lexitropsins and the in Vitro Inhibition of HIV–1 Reverse Transcriptase RNA–Directed DNA Polymerizaton: A Novel Induced–Fit of 3.5 m–Pyridyl Bisdistamycin to Enzyme–Associated Template–Primer, *Biochemistry*, (Dec. 3, 1996), 35:40, pp. 15399–15410.

Kissinger et al., Molecular Recognition between Oilgopeptides and Nucleic Acids: DNA Binding Specificity of a Series of Bis Netropsin Analogues Deduced from Footprinting Analysis, *Chem. Res. Toxicol.*, 3(2), (1990), pp. 162–168.

Neamati, Nouri et al., Highly Potent Synthetic Polyamides, Bisdistamycins, and Lexitropsins as Inhibitors and Human Immunodeficiently Virus Type 1 Integrase, *Molecular Pharmacology*, 54, (1998), pp. 280–290.

Wang, Z., et al., Effects of Bifunctional Netropson–related Minor Groove–binding Ligands on Mammallan Type I DNA Topolsomarase., *Biochem. Pharmacol.*, 53, (1997), pp. 309–316.

Buchwald, et al., A Highly Active Catalyst for Palladium–Catalyzed Cross–Coupling Reactions: Room–Temperature Suzuki Couplings and Amination of Unactivated Aryl Chlorides., *J. Am. Chem. Soc.*, 120, (1998), pp. 9722–9723.

Tidwell, R., et al., Anti–Pneumocystis carinil pneumonia activity of dicationic carbazoles, *Eur. J. Med. Chem.*,32, (1997), pp. 781–793.

Tidwell, R., et al., Dicationic dibenzofuran derivatives as anti-*Pneumocystis carinil* pneumonia agents: synthesis, DNA binding affinity, and anti–P, carinil activity in an immunosuppressed rat model, *Eur. J. Med. Chem.*, 34, (1999), pp. 215–224.

Bally, et al., Distribution of Furamidine Analogues in Tumor Cells: Influence of the Number of Positive Charges, *J. Med. Chem.*, 45(10), (2002), pp. 1994–2002.

Tidwell, Richard R., et al., Comparative efficacy evaluation of dicationic carbazole compounds, nitazoxanide, and paromomycin against *Crytoaporidium parvum* infections in a neonatal mouse model., *Antimicrob. Agents Chemother.*, (1998), 42(11). pp. 2877–2882.

Perfect, John R., et al., In vitro antifungal activities of a series of dication–substituted carbazoles, furans, and benzimidazoles, *Antimicrob. Agents Chemother*, (1998), 42(10), pp. 2503–2510.

* cited by examiner

*Primary Examiner*—Rita Desai
*Assistant Examiner*—Robert Shiao
(74) *Attorney, Agent, or Firm*—Junrui Yang

(57) ABSTRACT

This invention provides novel compounds possessing antibacterial and/or antifungal and/or antitumor activity. Pharmaceutical compositions containing these compounds, methods of making and methods for using these compounds are also provided.

8 Claims, No Drawings

ARYL AND HETEROARYL COMPOUNDS AS ANTIBACTERIAL AND ANTIFUNGAL AGENTS

CROSS-REFERENCE TO RELATED APPLICATIONS

This application claims the benefit under 35 U.S.C. 119(e) of U.S. Provisional Application Ser. No. 60/381,941, which was filed on May 16, 2002, the disclosure of which is incorporated herein in its entirety.

BACKGROUND OF THE INVENTION

1. Field of the Invention

This invention provides novel compounds possessing antibacterial, antifungal and/or antitumor activity. Pharmaceutical compositions containing these compounds, methods of making and methods for using these compounds are also provided.

2. State of the Art

The binding of the antibacterial netropsin and distamycin to AT-rich sequences in the minor groove of double-stranded DNA is a well studied phenomenon. Because such binding can be used to regulate DNA expression, e.g., by blocking and/or displacement of regulatory proteins, or by inhibiting the activity of enzymes acting on DNA, such as reverse transcriptase or topoisomerase, enhancement of this binding has been the subject of numerous recent studies.

As described in a recent review by Bailly and Chaires (*Bioconj. Chem.* 9(5):513–38, 1998), the pyrrolecarboxamide unit in netropsin and distamycin is actually about 20% longer than required to perfectly match the corresponding base pair sequence in the minor groove. Accordingly, in oligomeric analogs having multiple binding moieties, successive binding moieties can become out of phase with the base pairs of the minor groove. Several studies have therefore been directed to dimers of netropsin or distamycin containing different linkers, in order to improve binding to longer target sequences. In these reports, effectiveness of various netropsin or distamycin dimers was determined, for example, in the inhibition of transcription by HIV-1 reverse transcriptase (M. Filipowsky et al., *Biochemistry* 35:15397–410, 1996), inhibition of mammalian DNA topoisomerase I (Z. Wang et al., *Biochem. Pharmacol.* 53:309–16, 1997), or inhibition of HIV 1 integrase (N. Neamati et al., *Mol. Pharmacol.* 54:280–90, 1998).

Preferred linkers in these studies included p-phenylene, trans-vinyl, cyclopropyl, 3,5-pyridyl, and six- and eight-carbon aliphatic chains. Several of these linkers restrict rotation around the linking group, thus reducing the extent of purely monodentate binding (e.g. by only one netropsin moiety; see Bailly) which can occur with flexible linkers. However, Kissinger et al. (*Chem. Res. Toxicol.* 3(2): 162–8, 1990) reported that aryl-linked groups had reduced DNA binding affinity compared to alkyl and alkylene linkers, and Neamati et al. (cited above) reported that the trans-vinyl linked compound was many times more potent (in inhibiting HIV-1 integrase) than the "more rigid" cyclobutanyl and norbornyl linkers. It was suggested in Wang and in Bailly that, for certain applications, the more rigid linkers (cyclopropyl and p-phenylene) may not allow for optimal simultaneous (bidentate) binding of the two netropsin moieties flanking the linker. Therefore, it would be desirable to provide linkers which reduce monodentate binding but which provide suitable geometries for bidentate binding. Nevertheless, there is much confusion as to what constitutes linkers of choice such that highly active anti-bacterial compounds are formed.

Broadly, known antibacterial compounds work by influencing at least one of the following: cell wall synthesis, protein synthesis, nucleic acid synthesis, cellular metabolism and cytoplasmic membrane permeability. However, increasing resistance of bacteria to antibiotics has brought renewed attention to the development of new compounds that react against a broad array of common bacterial pathogens. Further, there has been increasing incidences of systematic fungal infections. The increase could be attributed to the chronic use of antimicrobial agents, lending to the realization that there is a need for new compounds to combat such infections. The compounds of the present invention fulfill this need.

SUMMARY OF THE INVENTION

This invention provides novel compounds which possess antibacterial, antifungal and/or antitumor activity. Specifically, the compounds of this invention are represented in Formula (I) below:

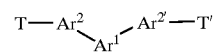

wherein each of $Ar^1$, $Ar^2$ and $Ar^{2'}$ are independently selected from the group consisting of aryl, substituted aryl, heteroaryl and substituted heteroaryl;

T and T' are independently selected from the group consisting of amido, aminoamido, carboxyl, carboxyl ester, amidino, and guanidino;

and further wherein the compounds of Formula I have an MIC of about 50 μM or less when tested for growth inhibition of at least one of the organisms selected from the group consisting of *Candida, Aspergillus, Enterococcus, Staphylococcus, Pseudomonas, Bacillus, Haemophilus, Streptococcus* and *Moraxella,* provided that

1) $Ar^1$ is not furanylene; and 2) both $Ar^2$ and $Ar^{2'}$ are not benzimidazolylene and further provided that the compound is not selected from the group consisting of:

2,5-bis(4-amidinophen-1-yl)-1H-pyrrole 2,5-bis(4-amidinophen-1-yl)-1-methyl-pyrrole 1,4-bis[5-(methoxycarbonyl)-thiophen-2-yl]benzene 1,4-bis[5-(methoxycarbonyl)-benzofuran-2-yl]benzene.

In another aspect, this invention provides for compounds selected from the group consisting of compounds of Formulae II, III, and IV:

a)

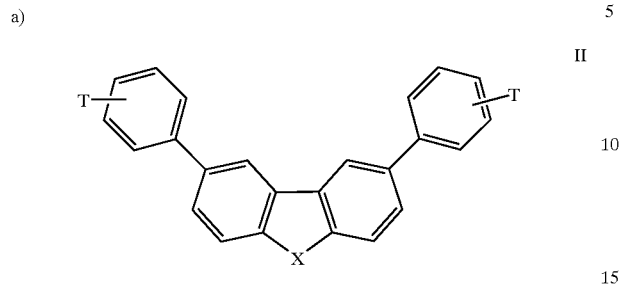

II wherein
X=N, O, or S, and
T is selected from the group consisting of amido, aminoamido, carboxyl, carboxyl ester, amidino and guanidino, b)

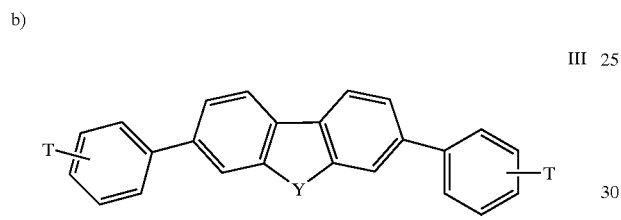

III wherein
Y=N, N=N, O, or S, and
T is selected from the group consisting of amido, aminoamido, carboxyl, carboxyl ester, amidino, and guanidino;
provided that the compound is not 2,7-bis{1-[N-(2-aminoeth-1-yl)-amido]phen-3-yl}-9H-carbazole
and c)

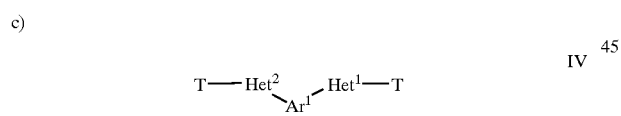

IV wherein
Het$^1$ and Het$^2$ are independently heteroaryl,
Ar$^1$ is aryl, heteroaryl, and
T is selected from the group consisting of amido, aminoamido, carboxyl, carboxyl ester, amidino, guanidino, with the provisos that
1) Ar$^1$ is not furanylene, and
2) Het$^1$ and Het$^2$ are not both benzimidazolylene, and
3) that the compound is not selected from the group consisting of 3,6-di[1H-indol-5-yl-2-carboxylic acid (carbamoylmethylamide)]-9H-carbazole,
1,4-bis{2-[N-(2-aminoeth-1-yl)-amido]-1H-indol-5-yl}benzene,
1,4-bis[5-(methoxycarbonyl)thiophen-2-yl]benzene, and
1,4-bis[5-(methoxycarbonyl)benzofuran-2-yl]benzene.

In formula I above, preferred Ar$^1$ groups include, for example, the following:

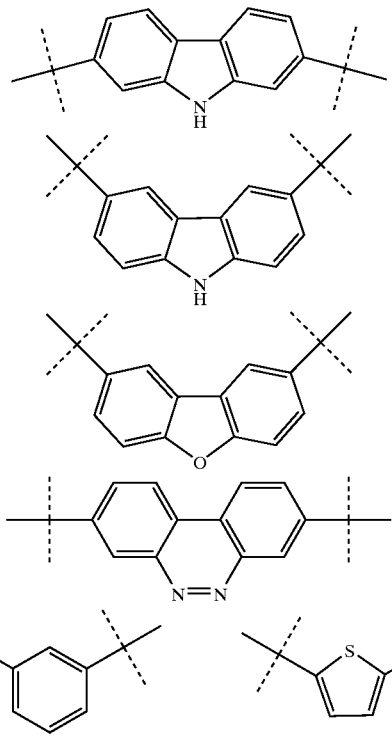

In formula I above, preferred Ar$^2$ and Ar$^{2'}$ groups independently include, for example, the following:

I

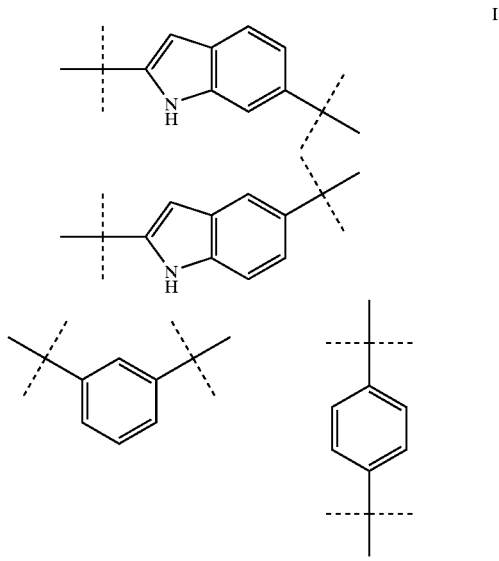

In formula I above, preferred T and T' groups independently include, for example, the following:

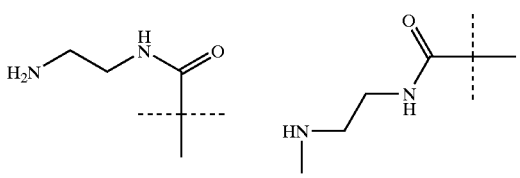

US 6,951,880 B2
5
-continued
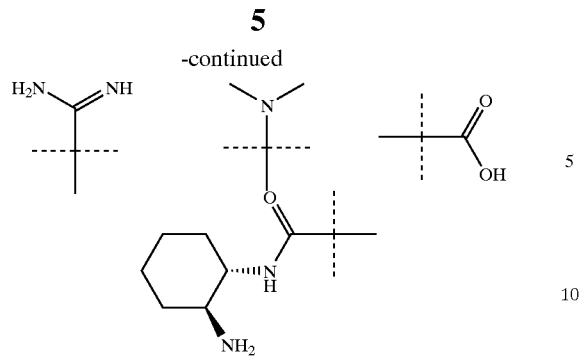
6
-continued
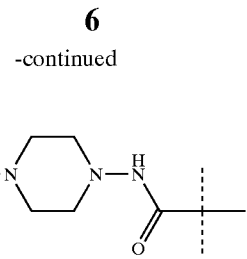
Particularly preferred compounds of formula I above are set forth in the following table:
| Ar¹ | Ar² | T |
|---|---|---|
| 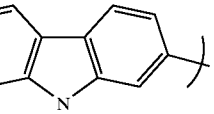 | 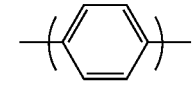 | 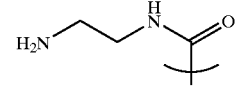 |
| 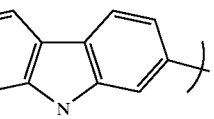 | 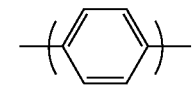 | 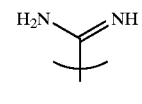 |
| 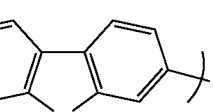 | 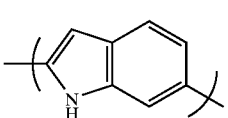 | 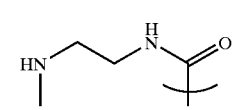 |
| 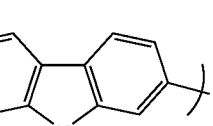 | 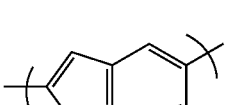 | 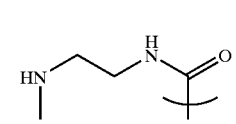 |
| 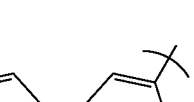 | 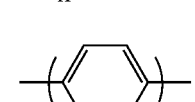 | 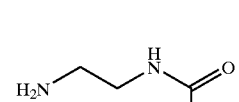 |
| 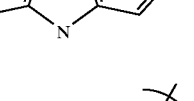 |  | 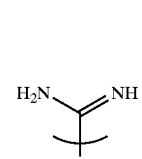 |
| 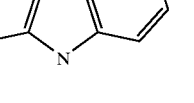 |  |  |
T—Ar²—Ar¹—Ar²—T

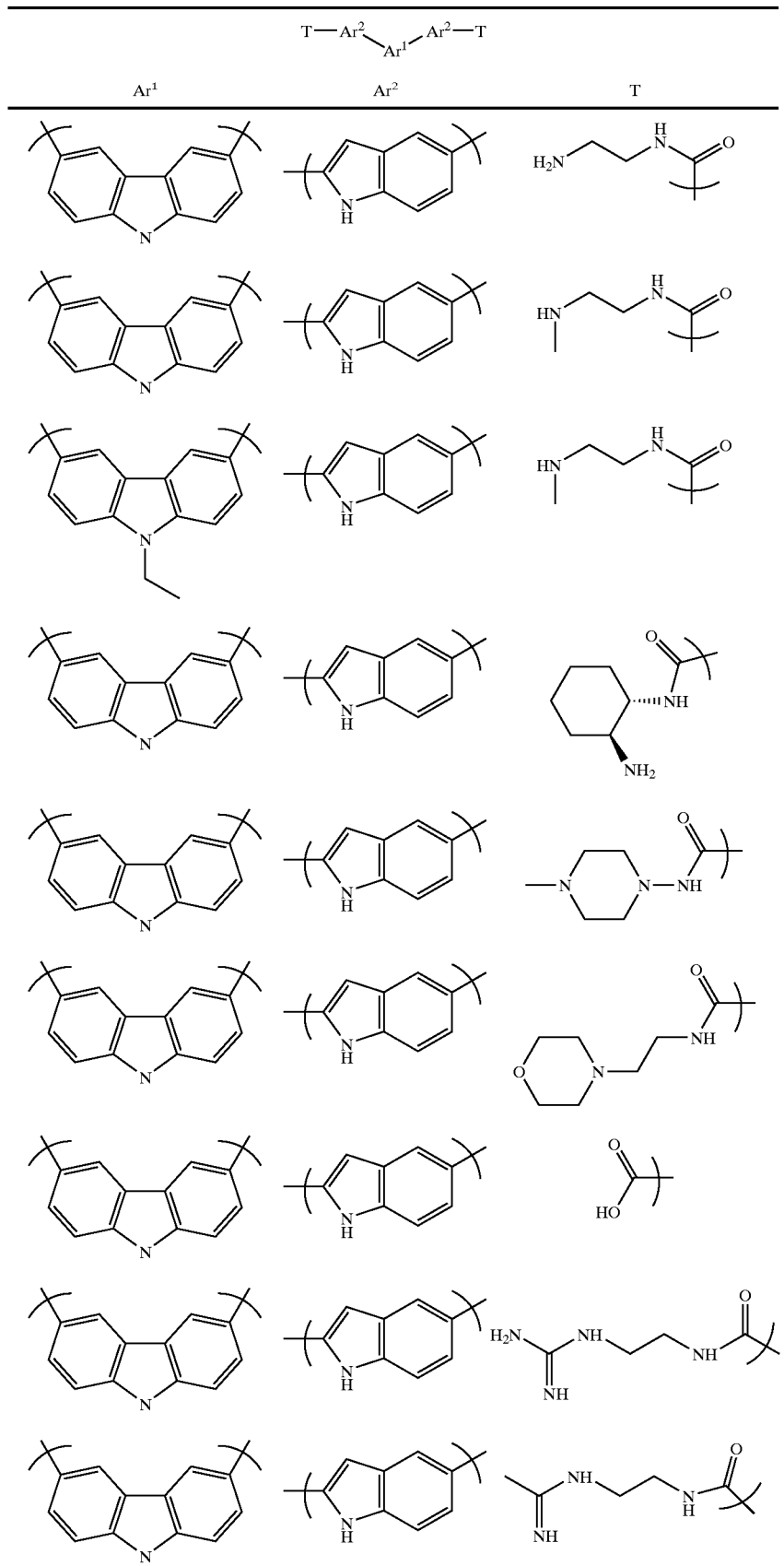

-continued

| Ar¹ | Ar² | T |
|---|---|---|
| 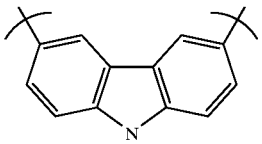 | 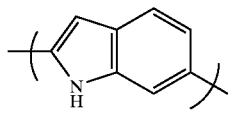 | 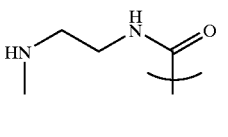 |
| 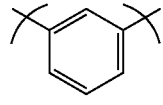 | 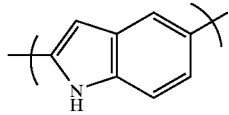 | 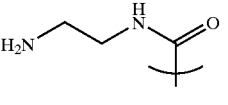 |
| 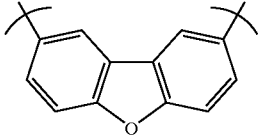 | 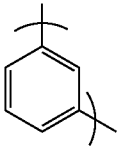 | 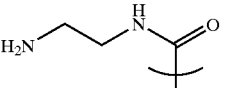 |
| 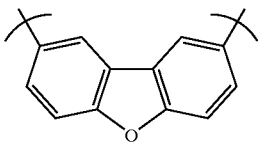 | 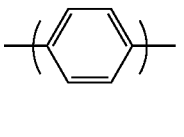 | 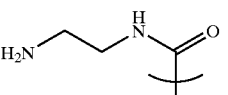 |
| 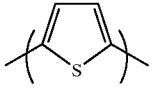 | 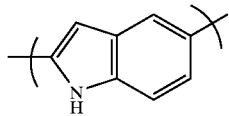 | 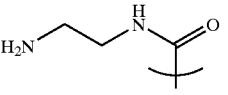 |
| 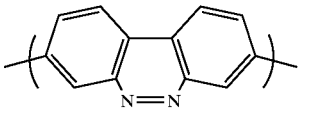 | 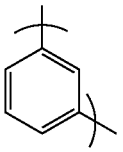 | 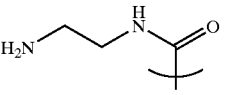 |

Specific compounds within the scope of this invention include the following:

3,6-bis{2-[N-(2-acetamidinoeth-1-yl)amido]-1H-indole-5-yl}-9H-carbazole
1,3-bis{2-[N-(2-aminoeth-1-yl)amido]-1H-indole-5-yl}benzene;
3,6-bis{2-[N-(2-aminoeth-1-yl)amido]-1H-indole-5-yl}9H-carbazole;
2,5-bis{2-[N-(2-aminoeth-1-yl)amido]-1H-indole-5-yl}thiophene;
2,8-bis{1-[N-(2-aminoeth-1-yl)amido]phen-3-yl}dibenzofuran;
3,8-bis{1-[N-(2-aminoeth-1-yl)amido]phen-3-yl}benzo[c]cinnoline;
2,7-bis{1-[N-(2-aminoeth-1-yl)amido]phen-4-yl}9H-carbazole;
3,6-bis{1-[N-(2-aminoeth-1-yl)amido]phen-3-yl}9H-carbazole;
2,8-bis{1-[N-(2-aminoeth-1-yl)amido]phen-4-yl}dibenzofuran;
3,6-bis{2-[N-(2-methylaminoeth-1-yl)amido]-1H-indol-5-yl}-9H-carbazole;
3,6-bis{1-[N-(2-aminoeth-1-yl)amido]phen-4-yl}-9H-carbazole;
3,6-bis[benzamidin-4-yl]-9H-carbazole;
2,7-bis[benzamidin-4-yl]-9H-carbazole;
3,6-bis{2-[N-(2-(morpholin-N-yl)eth-1-yl)amido]-1H-indol-5-yl}-9H-carbazole;
3,6-bis{2-[N-(2-aminocyclohex-1-yl)amido]-1H-indol-5-yl}-9H-carbazole;
3,6-bis{2-[N-(4-methylpiperazin-1-yl)amido]-1H-indol-5-yl}-9H-carbazole;
3,6-bis(1H-indol-5-yl)-9H-carbazole-2',2''-dicarboxylic acid;
2,7-bis{2-[N-(2-methylaminoeth-1-yl)amido]-1H-indol-5-yl}-9H-carbazole;
2,7-bis{2-[N-(2-methylaminoeth-1-yl)amido]-1H-indol-6-yl}-9H-carbazole;
3,6-bis{2-[N-(2-methylaminoeth-1-yl)amido]-1H-indol-6-yl}-9H-carbazole;
3,6-bis{2-[N-(2-methylaminoeth-1-yl)amido]-1H-indol-5-yl}-9-ethyl-carbazole;

3,6-bis{2-[N-(2-guanidinoeth-1-yl)amido]-1H-indol-5-yl}-9H-carbazole;
and pharmaceutically acceptable salts thereof.

In another aspect, this invention provides for pharmaceutical compositions comprising a therapeutically effective amount of a compound as described above and a pharmaceutically acceptable carrier.

In one of its method aspects, this invention provides for the treating or ameliorating an infection caused by pathogenic organisms, which method comprises administering to a mammal in need of such treatment a therapeutically effective amount of a pharmaceutical composition containing a therapeutically effective amount of a compound as described above and a pharmaceutically acceptable carrier.

DETAILED DESCRIPTION OF THE INVENTION

This invention is directed to novel compounds possessing antibacterial, antifungal and/or antitumor activity. However, prior to describing this invention in further detail, the following terms will first be defined.

Unless otherwise stated, the following terms used in the specification and claims have the meanings given below.

As used herein, "alkyl" refers to alkyl groups having from 1 to 5 carbon atoms and preferably 1 to 3 carbon atoms. This term is exemplified by groups such as methyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxylalkyl, carboxyl-substituted alkyl, carboxylaryl, carboxyl-substituted aryl, cycloalkyl, substituted cycloalkyl, heteroaryl, substituted heteroaryl, heterocyclic, and substituted heterocyclic.

"Alkoxy" refers to the group "alkyl-O-" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O-".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)- cycloalkyl-C(O)—, substituted cycloalkyl-C(O)—, aryl-C(O)—, substituted aryl-C(O)—, heteroaryl-C(O)—, substituted beteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" or "amido" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein, provided that both R' and R" are not hydrogen.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group having from 2 to 6 carbon atoms and preferably 2 to 4 carbon atoms and having at least 1 and preferably from 1–2 sites of alkenyl unsaturation.

"Substituted alkenyl" refers to alkenyl groups having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxylalkyl, carboxyl-substituted alkyl, carboxylaryl, carboxyl-substituted aryl, cycloalkyl, substituted cycloalkyl, heteroaryl, substituted heteroaryl, heterocyclic, and substituted heterocyclic.

"Alkynyl" refers to alkynyl group having from 2 to 6 carbon atoms and preferably 2 to 3 carbon atoms and having at least 1 and preferably from 1–2 sites of alkynyl unsaturation.

"Substituted alkynyl" refers to alkynyl groups having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxylalkyl, carboxyl-substituted alkyl, carboxylaryl, carboxyl-substituted aryl, cycloalkyl, substituted cycloalkyl, heteroaryl, substituted heteroaryl, heterocyclic, and substituted heterocyclic.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

"Substituted aryl" refers to aryl groups which are substituted with from 1 to 3 substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxylalkyl, carboxyl-substituted alkyl, carboxylaryl, carboxyl-substituted aryl, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings as defined above for substituted aryl.

"Carboxyl" refers to —COOH or salts thereof.

"Carboxylalkyl" refers to —C(O)Oalkyl where alkyl is as defined herein.

"Carboxyl-substituted alkyl" refers to —C(O)O-substituted alkyl where substituted alkyl is as defined herein.

"Carboxylaryl" refers to —C(O)Oaryl where aryl is as defined herein.

"Carboxyl-substituted aryl" refers to —C(O)O-substituted aryl where substituted aryl is as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to an cycloalkyl group, having from 1 to 5 substituents selected from the group consisting of oxo (=O), thioxo (=S), alkoxy, substituted alkoxy, acyl, acylamino, acyloxy, amino, aminoacyl, aryl, substituted aryl, aryloxy, substituted aryloxy, cyano, halogen, hydroxyl, nitro, carboxyl, carboxylalkyl, carboxyl-substituted alkyl, carboxylaryl, carboxyl-substituted aryl, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is either chloro or bromo.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl, imidazolyl and furyl.

"Substituted heteroaryl" refers to heteroaryl groups which are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, oxindole, azepine, diazepine, benzofuran, dibenzofuran and the like.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl.

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Aminoamido" refers to the group —C(O)NRNR'R" where R is hydrogen or alkyl, R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic, substituted heterocyclic, heteroaryl or substituted heteroaryl group provided that R' and R" are both not hydrogen and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to groups with the formula —C(=NR''')NR'R" where R', R" and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic, substituted heterocyclic, heteroaryl or substituted heteroaryl group. The term amidino also refers to reverse amidino structures of the formula

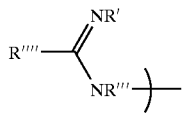

where R"" is an alkyl or substituted alkyl group as defined above and R''' and R' are as defined above.

"Guanidino" refers to groups with the formula —NHC(=NR''')NR'R" where R', R" and R''' are as defined above for amidino.

"Sulfonylamino" means a radical —NRSO$_2$R''' where R is hydrogen or alkyl and R''' is alkyl, substituted alkyl, amino, substituted amino, aryl, substituted aryl, heteroaryl, and substituted heteroaryl. Such groups include, for instance methylsulfonylamino, benzylsulfonylamino, N-methylaminosulfonylamino, and the like.

"Optional" or "optionally" means that the subsequently described event or circumstance may but need not occur, and that the description includes instances where the event or circumstance occurs and instances in which it does not. For example, "heterocyclic group optionally mono- or di-substituted with an alkyl group" means that the alkyl may but need not be present, and the description includes situations where the heterocyclic group is mono- or disubstituted with an alkyl group and situations where the heterocyclic group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R— and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable acid addition salts" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Groups which form pharmaceutically acceptable acid addition salts include amines, hydrazines, amidines, guanidines, substituted aryl/heteroaryl and substituted alkyl groups that carry at least a nitrogen bearing substituents such as amino, guanidine, amidino, hydrazine and the like.

A compound of Formula (I) may act as a pro-drug, which means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., amidoxime, acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Anti-fungal" or "anti-bacterial" means that growth of the fungi or bacteria is inhibited or stopped.

"Anti-tumor" means the compound has the property of inhibiting the growth of tumor cells. Preferably, when the compound is contacted with a tumor cell line at a concentration of 100 μM, growth of the tumor cells is 32% or less as that of a no growth control.

"Bacteriostatic" means the compound has the property of inhibiting bacterial or fungal growth, wherein growth resumes upon removal of the active compound. For a bacteriostatic compound, its minimum bacteriocidal concentration (MBC) is greater than 4× its minimum inhibitory concentration (MIC).

"Bacteriocidal" or "fungicidal" means that the compound has the property of killing bacteria or fungi. Bacteriocidal/fungicidal action differs from bacteriostasis or fungistasis only in being irreversible. For example, the "killed" organism can no longer reproduce, even after being removed form contact with the active compound. In some cases, the active compound causes lysis of the bacterial or fungal cell; in other cases the bacterial or fungal cell remains intact and may continue to be metabolically active. A bacteriocidal compound exhibits a MBC that is less than 4× its MIC. Similarly, a fungicidal compound exhibits a minimum fungicidal concentration (MFC) that is less than 4× its MIC.

"Minimum inhibitory concentration" or "MIC" refers to the minimum concentration of a compound necessary to inhibit growth of the organism tested. Compounds of this invention having an MIC 1 mM or less are active in the assays described in the examples below. In a preferred embodiment compounds have an MIC of 500 µM, and even more preferably an MIC of 100 µM and even more preferably an MIC of 50 µM.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Compounds of the present invention may be made using procedures well known in the art, which are represented schematically in Schemes I (symmetric) and 2 (asymmetric) below.

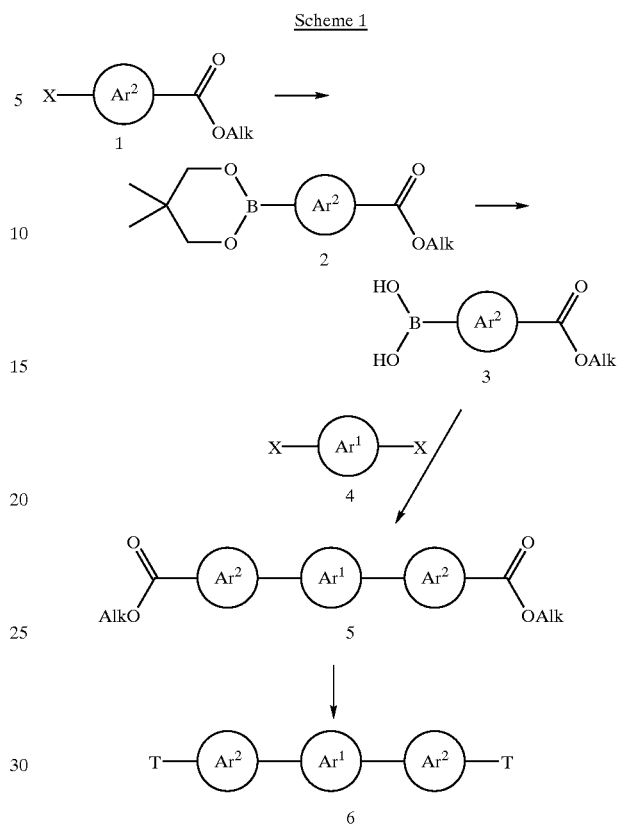

Scheme 1 where Alk is an alkyl or substituted alkyl group (e.g., benzyl), X is halo, $Ar^2$, $Ar^1$ and T are as defined above.

In Scheme 1, the synthesis of symmetric compounds, 6, is shown. Specifically, a haloaryl or haloheteroaryl carboxylate ester, 1, is converted to the boronic acid ester, 2, by contacting 1 with at least a stoichiometric amount and preferably an excess of a boronic acid ester such as bis (neopentylglycolato) diboron (not shown). The reaction is preferably conducted in an inert solvent such as dioxane, dimethylsulfoxide (DMSO), tetrahydrofuran, toluene and the like. The reaction is conducted in the presence of an excess of potassium acetate and a catalytic amount of palladium reagent such as bis-(triphenylphosphine) palladium dichloride, tetrakis(triphenylphosphine) palladium and the like. The reaction mixture is typically maintained at an elevated temperature of from about 50 to about 100° C. until reaction completion which typically occurs in about 2 to 16 hours. The resulting boronic acid ester, 2, can be purified by conventional techniques such as filtration, precipitation, chromatography and the like or used in the next step of the reaction scheme without purification and/or isolation.

The boronic acid ester, 2, is next converted to the corresponding boronic acid, 3, which includes a mixture of anhydrides (not shown), by contacting the ester with diethanolamine in the presence of solvent mixtures such as methanol, ethanol, isopropanol and the like in ether to effect transesterification from the neopentyl glycolato ester to the diethanolamine ester. Preferably, the solvent is a 1:5 mixture of methanol:diethyl ether. In another preferred embodiment, the diethanolamine is combined with solvent and then added in aliquots to the mixture of boronic acid ester and solvent. In a particularly preferred embodiment, the solvent used with the diethanolamine is the same as that used to dissolve the boronic acid ester. The reaction mixture is typically maintained at from about 10 to about 40° C. until reaction completion which typically occurs in about 0.1 to 2 hour upon which the diethanolamine boronic acid ester (not shown) precipitates from solution. Precipitation is facilitated by the ratio of protic solvent:diethyl ether present which can be adjusted to enhance precipitation.

The precipitate is filtered and the collected solids are washed and then contacted with a concentrated aqueous acidic solution, e.g., 6N HCl. The resulting mixture is stirred for 2 to 24 hours at room temperature or below (0 to 25° C.) upon which the boronic acid, 3, can be recovered by, for example, filtration.

Coupling of the reagents 3 and 4 is a modified Suzuki reaction which is described by, for example, Buchwald, et al., *Journal American Chemical Society*, (1998) 120:9722. Specifically, at least 2 equivalents of the boronic acid, 3, is contacted with a dihaloaryl or heteroaryl compound, 4. The reaction is conducted in an inert solvent such as toluene, dimethoxyethane, dioxane, tetrahydrofuran, and the like in the presence a base such as cesium carbonate, cesium fluoride, potassium t-butoxide, potassium phosphate, sodium bicarbonate and the like, and further in the presence of a catalytic amount of a palladium compound such as palladium(II)acetate, bis(triphenylphosphine)palladium chloride, tetrakis(triphenylphosphine)palladium, tris (dibenzylideneacetone)dipalladium and the like as well as a catalytic amount of a phosphine ligand such as dicyclohexyl-phosphinobiphenyl, triphenylphosphine and the like. The reaction is typically maintained at from 20 to 100° C. and preferably at elevated temperatures of from about 40 to 100° C. until reaction completion which typically occurs in about 10 to 60 hours. The resulting diester, 5, can be purified by conventional techniques such as filtration, precipitation, chromatography and the like or used in the next step of the reaction scheme without purification and/or isolation.

Diester, 5, is then converted to compound 6 by conventional techniques well known in the art. For example, compounds where each T is a carboxyl group are prepared by hydrolysis of the diester. Compounds where T is a carboxyl ester can be prepared by transesterification of the diester, 5. Compounds where T is an amido, aminoamido, or aminoalkylamido group can be prepared by conventional reaction of an amine, hydrazine, or alkylenediamine compound with the carboxylic acid optionally in the presence of well known coupling reagents such as the BOP reagent [benzotriazol-1-yloxy-tris(dimethylamino)phosphonium hexafluorophosphonate)], suitable carbodiimides such as dicyclohexyl-carbodiimide (DCC), 1-(3-dimethylaminopropyl)-3-ethylcarbodiimide (EDC) and the like. Guanidinoalkylamido compounds are prepared starting from the previously described aminoalkylamido compounds by reaction with the appropriately derivatized pyrazolecarboxamidine and diisopropylethylamine hydrochloride salts.

Amidino groups are prepared similarly as above, but replacing the boronic acid ester, compound 2, shown in scheme 1, with the appropriate cyanoboronic acid ester. The cyano group replaces the carboxylic acid ester. The cyano group is then converted to the amidino group using methods well known in the art. For example, using a saturated HCl/EtOH solution at 0 to 30° C. for 24–36 hrs. The solvent is then removed and the remaining solid co-evaporated with ethanol once to remove any remaining HCl followed by the addition of saturated NH$_3$/EtOH at or about room temp for 2 to 3 days. The resulting diamidino compound can be purified by conventional techniques such as filtration, precipitation, chromatography and the like.

Alternatively, asymmetric compounds can be prepared as shown in Scheme 2 below:

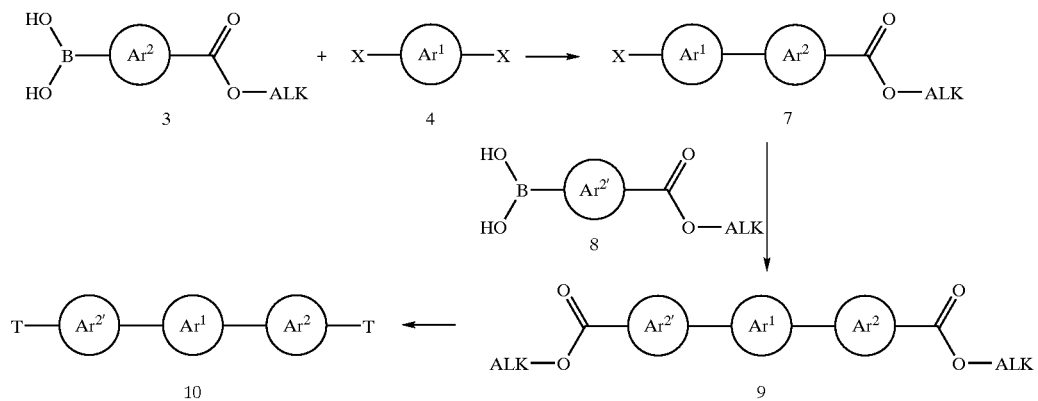

Coupling of reagents 3 and 4 is again a modified Suzuki reaction as described above with the exception that molar equivalents of 3 and 4 or an excess of 4 are employed in order to favor formation of dimer 7 rather than trimer 5. Nevertheless, a mixture of dimer, trimer (7 and 5 respectively) as well as unreacted monomer is formed which can be purified by conventional techniques such as filtration, precipitation, chromatography and the like or used in the next step of the reaction scheme without purification and/or isolation.

Dimer 7 is converted to trimer 9 by reaction with a stoichiometric equivalent or excess thereof of reagent 8 again following the modified Suzuki reaction described above. Trimer 9, can be purified by conventional techniques such as filtration, precipitation, chromatography and the like or used in the next step of the reaction scheme without purification and/or isolation.

As is apparent, Scheme 2 permits the formation of non-symmetric Ar$^2$ and Ar$^{2'}$ groups coupled to the Ar$^1$ in formula I. Additionally, Scheme 2 permits formation of non-symmetric T groups by, for example, using an —O-Alk group in reagent 3 which is differentially removed than the —O-Alk group in reagent 8. For example, use of an —O-benzyl group in reagent 3 and an —O-methyl group in reagent 8 allows for differential removal of the methyl group by hydrolysis and subsequent formation of a suitable T group while retaining the —O-benzyl group until its removal by hydrogenation and subsequent formation of a suitable T' group where T≠T'.

The preparation of haloaryl or haloheteroaryl carboxylic acid esters, compound 1, is well known in the art and some of these compounds are commercially available.

Similarly, the preparation of dihaloaryl or dihaloheteroaryl compound, 4, is well known in the art and many of these compounds are commercially available. The syntheses of 2,7-dibromocarbazole and 3,8-dibromobenzo[c]cinnoline compounds were accomplished as described in Eur. J. Med. Chem. (1999) 34, 215–224 and Eur. J. Med. Chem. (1997) 32, 781–793. The synthesis of 2,8-dibromobenzofuran was accomplished as described in J. Med. Chem., (1985) 28: 1728–1740.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of this invention associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other, ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compounds of this invention are employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
| --- | --- |
| Active Ingredient | 5.0 mg |
| Corn Oil | 1.0 mL |

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*, Mace Publishing Company, Philadelphia, Pa., 17th ed. (1985).

Utility

The compounds of this invention possess antibacterial, antifungal and/or antitumor activity and, accordingly, are useful in the treatment of bacterial infections, fungal infections and/or cancer. Some examples of bacterial or fungal organisms that can be treated by compounds of this invention include *Bacillus, Bacteroides, Bacteriodes vulgatus, Bordetella, Branhamella, Bukholderia, Campylobacter, Clostridium, Escherichia, Enterobacter, Enterococcus, Erysipelothrix, Eubacterium, Exterobacter, Haemophilus, Klebsiella, Leclercia, Listeria, Morexella,* MRSA (Methicillin Resistant *S. aureus*), *Neisseria, Plesiomonas, Porphyromonas, Propionibacterium, Proteus, Providencia, Pseudomonas, Seratia, Staphylococcus, Streptococcus,* VRE (Vancomycin resistant *Enterococci*), *Aspergillus, Blastomyces, Candida, Coccidioides, Cryptococcus, Fusarium, Histoplasma, Microsporum, Paraccidioides, Rhizopus, Scedosporium, Sporothrix, Torulopsis, Trichosporon,* and *Trichophyton.*

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of Formula (I) may range from approximately 0.05 to 200 mg per kilogram body weight of the recipient per day; preferably about 0.01–25 mg/kg/day, more preferably from about 0.5 to 10 mg/kg/day. Thus, for administration to a 70 kg person, the dosage range would most preferably be about 35–70 mg per day.

The following synthetic and biological examples are offered to illustrate this invention and are not to be construed in any way as limiting the scope of this invention. Unless otherwise stated, all temperatures are in degrees Celsius.

In the examples below, the following abbreviations have the following meanings. If an abbreviation is not defined, it has its generally accepted meaning.

g = gram
kg = kilogram
mg = milligram
μg = microgram
μM = micromolar
nM = nanomolar
mmol = millimole -continued

| | |
|---|---|
| mM = | millimolar |
| M = | molar |
| mol = | mole |
| mL = | milliliter |
| μL = | microliter |
| N = | normal |
| mm = | millimeter |
| nm = | nanometer |
| m = | meter |
| min = | minute |
| h = | hour |
| brd = | broad doublet |
| brm = | broad multiplet |
| brt = | broad triplet |
| bs = | broad singlet |
| conc. = | concentrated |
| dd = | doublet of doublets |
| DIEA = | diisopropylethyl amine |
| DMF = | N,N-dimethylformamide |
| DMSO = | dimethylsulfoxide |
| dt = | doublet of triplets |
| EDCI = | 1-(3-dimethylaminopropyl)-3-ethylcarbodiimide hydrochloride |
| eq. = | equivalents |
| HOAc = | acetic acid |
| HPLC = | high performance liquid chromatography |
| LC/MS = | liquid chromatography/mass spectroscopy |
| m = | multiplet |
| psi = | pounds per square inch |
| q = | quartet |
| rpm = | rotations per minute |
| rt = | room temperature |
| $R_t$ = | retention time |
| s = | singlet |
| t = | triplet |
| TEA = | triethylamine |
| TFA = | trifluoroacetic acid |
| THF = | tetrahydrofuran |
| TLC = | thin layer chromatography |
| mol % = | mol percent |
| HCl = | hydrochloric acid |
| $Et_2O$ = | diethylether |
| $H_2O$ = | water |
| MeOH = | methanol |
| EtOH = | ethanol |
| EtOAc = | ethyl acetate |
| KOAc = | potassium acetate |
| CsF = | cesium fluoride |
| NaOH = | sodium hydroxide |

EXAMPLES

The following preparations and examples are given to enable those skilled in the art to more clearly understand and to practice the present invention. They should not be considered as limiting the scope of the invention, but merely as being illustrative and representative thereof.

All compounds not specifically provided for in the following synthesis are commercially available from Aldrich Sigma, Lancaster, Biosynth AG, and Frontier Scientific.

Example 1
Preparation of 3,6-bis{2-[N-(2-guanidinoeth-1-yl)-amido]-1H-indol-5-yl}-9H-carbazole Step 1: A 250 mL round-bottom flask charged with 5 g (18.65 mmol) ethyl 5-bromoindolecarboxylate, 4.64 g (20.52 mmol) bis(neopentyl glycolato)diboron, and 5.49 g (55.95 mmol) potassium acetate was flushed with argon, and 0.39 g (0.56 mmol) $(Ph_3P)_2PdCl_2$ was added. Anhydrous DMSO (100 mL) was introduced and the mixture was stirred and heated at 80° C. under argon overnight. The mixture was cooled to room temperature, diluted with 300 mL ethyl acetate and filtered through celite. The filtrate was washed with 3×100 mL water, the organic phase was dried over sodium sulfate and the solvent was evaporated. The residue was purified on silica gel using hexane/ethyl acetate (gradient elution) to yield 4.85 g (86%) of the boronic acid ester.

$^1$H NMR__1.00 (s, 6H), 1.21 (t, J=7.1 Hz, 3H), 3.80 (s, 4H), 4.07 (q, J=7.2 Hz, 2H), 7.22 (m, 1H), 7.44 (d, J=8.4 Hz, 1H), 7.62 (d, J=8.4 Hz, 1H), 8.11 (s, 1H).

Step 2: 2-Ethoxycarbonylindole-5-boronic acid neopentyl glycol ester (4.85 g, 16.11 mmol) was dissolved in a mixture of 25 mL MeOH and 125 mL $Et_2O$. Diethanolamine (2.03 g, 19.33 mmol) was dissolved in 25 mL MeOH and the solution was diluted with 125 mL $Et_2O$. The diethanolamine solution was added to the solution of the boronic ester in 1 mL portions while stirring. The mixture was stirred for 1 h and the precipitate was separated, washed with $Et_2O$ and air-dried. The powder was suspended in 300 mL water and 15 mL of 6 N aqueous HCl solution was added to the suspension while stirring. The suspension was stirred overnight, filtered, and the solids were washed with $H_2O$ and air-dried to yield 2.11 g (56%) of 2-Ethoxycarbonylindole-5-boronic acid, which was not analytically characterized due to the mixture of anhydrides it is known to form.

Step 3: A representative procedure for the mono-phasic bis-cross coupling reaction of bis-arylhalides with boronic acids is a modification of cross coupling reactions described by Buchwald, et al (*J. Am. Chem. Soc.* 1998, 120, 9722–9723). 3,6-Dibromocarbazole (1.52 g, 4.69 mmol), 2.73 g (11.72 mmol) 2-ethoxycarbonylindole-5-boronic acid, and 5.34 g (35.16 mmol) CsF were dissolved in 50 mL anhydrous dioxane under argon. $Pd(OAc)_2$ (106 mg, 0.47 mmol) and 245 mg (0.70 mmol) dicyclohexylphosphinobiphenyl were dissolved in 20 mL dioxane under argon and added to the above mixture. The resulting mixture was stirred and refluxed under argon overnight, cooled to room temperature, diluted with 200 mL EtOAc and filtered through celite. The filtrate was washed with 3×75 mL $H_2O$. The organic phase was dried over sodium sulfate and the solvent was evaporated. The residue was purified by flash-column chromatography using hexane/EtOAc (7:3–6:4) as eluent to yield 1.07 g (46%) of 3,6-Bis(5-indolyl)carbazole-2',2'-dicarboxylic acid diethyl ester.

$^1$H NMR__1.41 (t, J=6.9 Hz, 6H), 4.41 (q, J=7.2 Hz, 4H), 7.26 (d, J=1.8 Hz, 2H), 7.59 (s, 2H), 7.62 (s, 2H), 7.77 (m, 2H), 7.80 (m, 2H), 8.08 (d, J=0.9 Hz, 2H), 8.61 (d, J=1.2 Hz, 2H), 11.34 (s, 1H), 11.96 (s, 2H).

Step 4: 3,6-Bis-(5-indolyl)carbazole-2',2'-dicarboxylic acid diethyl ester (0.7 mmol) was dissolved in 3.5 mL ethylenediamine in an amber glass vial with a Teflon screw-cap and heated at 55° C. in a sand-bath overnight. The excess amine was removed under vacuum and the residue was dissolved in 7 mL DMSO, 0.7 mL TFA was added and the solution was added up to 35 mL by $H_2O$. The solution was purified by preparative HPLC in 7 injections. Fractions containing 3,6-Bis-(5-indolyl)carbazole-2',2'-bis(2-aminoethyl) carboxamide were pooled and evaporated. The residues were combined and used in the next step as such.

Step 5: 3,6-Bis-(5-indolyl)carbazole-2',2'-bis(2-aminoeth-1-yl)carboxamide bistrifluoroacetate (0.5 mmol) was mixed with 2.5 mL DMF, 10 mmol diisopropylethyamine and 5 mmol pyrazole-1-carboxamidine hydrochloride were added and the resulting solution was heated at 55° C. for 24 hr. The solvent was removed under vacuum and the residue was dissolved in 5 mL DMSO, 0.5 mL TFA was added and the solution was added up to 25 mL by $H_2O$. The solution was purified by preparative HPLC in 5 injections. Appropriate fractions were pooled and evaporated. The residue was dissolved in 5 mL MeOH, divided into 5 centrifuge tubes and cooled in dry ice for 5 min. One mL of 2 N HCl solution in dioxane was added to each tube and the solutions were immediately diluted to 40 mL each by cold $Et_2O$. The suspensions were centrifuged and the supernatant liquids were decanted. The cakes were dissolved in 1 mL MeOH each and precipitated with cold $Et_2O$. The suspensions were centrifuged and the supernatant liquids were decanted. The residues were dissolved in water and lyophilized to yield 3,6-bis{2-[N-2-guanidinoeth-1-yl)amido]-1H-indol-5-yl}-9H-carbazole.

Example 2

Preparation of 3,6-bis(2-(1-methylamino-2-ethylaminocarbonyl)-1H-indol-5-yl)-9H-carbazole dihydrochloride Steps 1–3 were identical to Steps 1–3 of Example 1.

Step 4: 3,6-Bis(5-indolyl)carbazole-2',2'-dicarboxylic acid diethyl ester (0.38 g, 0.70 mmol) was dissolved in 3.5 mL N-methylethylenediamine in an amber glass vial with a Teflon screw-cap and heated at 55° C. in a sand-bath for 72 h. The excess amine was removed under vacuum and the residue was dissolved in 7 mL DMSO, 0.7 mL TFA was added and the solution was added up to 35 mL by $H_2O$. The solution was purified by preparative HPLC in 7 injections. Appropriate fractions were pooled and evaporated. The residue was dissolved in 7 mL MeOH, divided into 7 centrifuge tubes and cooled in dry ice for 5 min. One mL of 2 N HCl solution in dioxane was added to each tube and the solutions were immediately diluted to 40 mL each by cold $Et_2O$. The suspensions were centrifuged and the supernatant liquids were decanted. The cakes were dissolved in 1 mL MeOH each and precipitated with cold $Et_2O$. The suspensions were centrifuged and the supernatant liquids were decanted. The residues were dried, dissolved in $H_2O$ and lyophilized to yield 134 mg (29%) of 3,6-bis(2-(1-methylamino-2-ethylamino-carbonyl)indol-5-yl)carbazole dihydrochloride.

$^1$H NMR_2.66 (s, 6H), 3.19 (m, 4H), 3.66 (m, 4H), 7.32 (s, 2H), 7.59 (m, 4H), 7.71 (d, J=8.7 Hz, 2H), 7.79 (d, J=8.4 Hz, 2H), 8.06 (s, 2H), 8.62 (s, 2H), 8.81–9.00 (m, 4H), 11.34 (s, 1H), 11.73 (s, 2H).

Example 3

Preparation of 3,6-bis-{1-[N-(2-aminoeth-1-yl)amido]phen-3-yl}-9H-carbazole 3,6-Dibromocarbazole (65 mg, 0.2 mmol) and anhydrous CsF (182 mg, 1.2 mmol) were added to an oven-dried reaction carousel vessel (24 mm×150 mm) containing a magnetic stir bar. The reaction vessel underwent vacuum/argon purge cycles 3 times. In a separate oven-dried argon purged 25 mL round bottom flask, 3-ethoxycarbonyl phenylboronic acid (116 mg, 0.6 mmol), $PdII(OAc)_2$ (4.5 mg, 10 mol %), dicyclohexylphosphinobiphenyl (10.5 mg, 15 mol %), and 1.5 mL de-gassed dioxane were charged. The resulting mixture was stirred for 10 min (solution turned black) then transferred to the reaction vessel containing halide and CsF. The reaction vessel was purged with argon, sealed with a rubber septum and heated at 80° C. for 48 h. The reaction mixture was diluted with toluene and passed through a pre-packed celite column which had been pre-wetted with water to half the volume of celite (Varian Chem Elute CE1005). The filtrate was dried over magnesium sulfate and concentrated in vacuo. The solid material was dissolved in ethylenediamine (2.0 mL) and placed in a 50° C. oven for 36 hours. The excess ethylenediamine was removed in vacuo and the crude product was dissolved in $DMSO:H_2O$, 0.1% TFA (4:1) and separated on reverse phase HPLC column (Vydac, $C_{18}$ column) with elution gradient 0–60% (Acetonitrile, 0.1% TFA: $H_2O$, 0.1% TFA). MS 246.62 [M+2H]/2.

Example 4

Preparation of 1,3-bis{2-[N-(2-aminoeth-1-yl)amido]-1H-indole-5-yl}benzene

The title compound was prepared as described in steps 1–4 of Example 1, using 1,3-dibromobenzene in step 3 in place of 3,6-dibromocarbazole.

Example 5

Preparation of 3,6-bis{2-[N-(2-aminoeth-1-yl)amido]-1H-indole-5-yl}-9H-carbazole The title compound was prepared as described in steps 1–4 of Example 1.

Example 6

Preparation of 2,5-bis{2-[N-(2-aminoeth-1-yl)amido]-1H-indole-5-yl}thiophene

The title compound was prepared as described in steps 1–4 of Example 1, using 2,5-dibromothiophene in step 3 in place of the 3,6-dibromocarbazole.

Example 7

Preparation of 2,8-bis-{1-[N-(2-amino-eth-1-yl)-amido-]phen-3-yl}dibenzofuran

The title compound was prepared as described in Example 3, using 2,8-dibromo-dibenzofuran in place of the 3,6-dibromocarbazole.

Example 8

Preparation of 3,8-bis{1-[N-(2-aminoeth-1-yl)amido]phen-3-yl}benzo[c]cinnoline

The title compound was prepared as described in Example 3, using 3,8-dibromocinnoline in place of the 3,6-dibromobenzo[c]cinnoline.

Example 9

Preparation of 2,7-bis{1-[N-(2-aminoeth-1-yl)amido]phen-4-yl}-9H-carbazole

The title compound was prepared as described in Example 3, using 2,7-dibromocarbazole and 4-methoxycarbonylphenyl boronicacid in place of the 3,6-dibromocarbazole and 3-ethoxycarbonylphenyl boronicacid.

Example 10

Preparation of 2,8-bis{1-[N-(2-aminoeth-1-yl)amido]phen-4-yl}dibenzofuran

The title compound was prepared as described in Example 3, using 2,8-dibromo-dibenzofuran in place of the 3,6-dibromocarbazole and 4-methoxycarbonyl phenylboronic acid in place of 3-ethoxycarbonyl phenylboronic acid.

Example 11

Preparation of 3,6-bis{1-[N-(2-aminoeth-1-yl)amido]phen-4-yl}-9H-carbazole

The title compound was prepared as described in Example 3, using 4-methoxycarbonyl phenylboronic acid in place of 3-ethoxycarbonyl phenylboronic acid.

Example 12

Preparation of 3,6-bis{2-[N-2-acetamidinoeth-1-yl)amido]-1H-indol-5-yl}-9H-carbazole The title compound was prepared as described in Example 1, using ethyl acetamidate hydrochloride in place of the pyrazole-1-carboxamidine hydrochloride in Step 5.

Example 13
Preparation of 2,7-bis[benzamidin-4-yl]-9H-carbazole
Step 1: The formation of 2,7-bis(4-cyanophenyl)carbazole is identical to Example 3 prior to the addition of ethylene diamine, using 2,7-dibromocarbazole and 4-cyanophenylboronic acid in place of 3,6-dibromocarbazole and 3-ethoxycarbonyl phenylboronic acid, respectively.
Step 2: The formation of 2,7-bis(4-amidinophenyl)carbazole was as follows: The crude 2,7-bis(4-cyanophenyl)carbazole was dissolved in 3 mL THF and diluted with 10 mL saturated HCl/EtOH solution. The reaction was allowed to stand at room temp for 48 h then the solvent was removed in vacuo. The resulting bisimidate ethylester was co-evaporated with ethanol once to remove any remaining HCl followed by the addition of 15 mL saturated $NH_3$/EtOH. The solution was allowed to stand at room temp for 48 h. The solvent was removed in vacuo and the crude amidine was dissolved in DMSO:$H_2O$, 0.1%TFA (4:1) and separated on a reverse phase HPLC column (Vydac, $C_{18}$ column) with elution gradient 0–60% ($H_2O$, 0.1% TFA: acetonitrile, 0.1% TFA). MS 202.59 [M+2H]/2.

Example 14
Preparation of 3,6-bis{2-[N-(2-(morpholin-N-yl)eth-1-yl)-amido]-1H-indol-5-yl}-9H-carbazole
Steps 1–3 Were the Same as Described for Example 1.
Step 4: 3,6-Bis(5-indolyl)carbazole-2',2'-dicarboxylic acid diethyl ester (0.90 g, 1.66 mmol) was dissolved in 25 mL THF. MeOH (20 mL) and 5 mL 2 M aqueous NaOH solution were added and the solution was stirred at 50° C. overnight. The organic solvents were removed and the residue was diluted with 45 mL $H_2O$. The solution was brought to pH 3 with 1 M HCl. 3,6-Bis(5-indolyl)carbazole-2',2'-dicarboxylic acid was collected by filtration, washed with $H_2O$ and dried in a dessicator under vacuum to yield 733 mg (91%) dark solids.
$^1$H NMR__7.21 (d, J=0.9, 2H), 7.59 (m, 4H), 7.77 (m, 4H), 8.07 (s, 2H), 8.62 (s, 2H), 11.33 (s, 1H), 11.84 (s, 2H).
Step 5: A mixture of 684 mg (1.41 mmol) 3,6-Bis(5-indolyl)carbazole-2',2'-dicarboxylic acid, 1.76 g (8.46 mmol) pentafluorophenyl trifluoroacetate and 1.09 g (8.46 mmol) diisopropylethylamine in DMF was allowed to stand at room temperature for 24 h. The volatiles were removed by high vacuum and the residue was purified on silica gel using hexane/EtOAc as eluent (gradient elution) to yield 1.15 g (100%) of activated 3,6-Bis(5-indolyl)carbazole-2',2'-dicarboxylic acid bis(pentafluorophenyl) ester.
Step 6: The PFP ester (0.1–0.2 mmol) was dissolved in 1 mL/0.1 mmol anhydrous DMF in a brown glass vial with a Teflon screw-cap. Ten equivalents of the appropriate amine [1-(N-morpholino)ethylamine] was added to the vial, 20 equivalents of diisopropylethylamine was used to neutralize any salt form of the amines, and the vial was kept in a 55° C. oven. The progress of the reaction was monitored by HPLC and at the end of the reactions (72 h) the solvent and excess amine were removed by vacuum. The residue was dissolved in 1 mL DMSO, 0.1 mL TFA was added and the solution was added up to 5 mL by $H_2O$. The solution was purified by preparative HPLC. Appropriate fractions were pooled and evaporated. The residue was dissolved in 1 mL MeOH and cooled in dry ice for 5 min. One mL of 2 N HCl solution in dioxane was added and the solution was immediately diluted to 40 mL by cold $Et_2O$. The suspension was centrifuged and the supernatant liquid was decanted. The cake was dissolved in MeOH and precipitated with cold $Et_2O$. The suspension was centrifuged and the supernatant liquid was decanted. The residue was dried, dissolved in $H_2O$ and lyophilized.

Example 15
Preparation of 3,6-bis{2-[N-(2-aminocyclohex-1-yl)-amido]-1H-indol-5-yl}-9H-carbazole
The title compound was prepared as described in Example 14, using 2(R),3(S)-diaminocyclohexane in place of 1-(N-morpholino)ethylamine.

Example 16
Preparation of 3,6-bis{2-[N-(4-methylpiperazin-1-yl)-amido]-1H-indol-5-yl}-9H-carbazole
The title compound was prepared as described in Example 14, using 4-methyl-1-aminopiperazine in place of the 1-(N-morpholino)ethylamine.

Example 17
Preparation of 3,6-bis(1-H-indol-5-yl)-9H-carbazole-2',2"-dicarboxylic acid
The title compound was prepared using only steps 1–4 as described in Example 14.

Example 18
Preparation of 2,7-bis{2-[N-(2-methylaminoeth-1-yl)-amido]-1H-indol-5-yl}-9H-carbazole
The title compound was prepared as described in Example 2, using 2,7-dibromocarbazole in place of 3,6-dibromocarbazole.

Example 19
Preparation of 2,7-bis{2-[N-(2-methylaminoeth-1-yl)-amido]-1H-indol-6-yl}-9H-carbazole
The title compound was prepared as described in Example 18, using ethyl 6-bromoindolecarboxylate in place of ethyl 5-bromoindolecarboxylate.

Example 20
Preparation of 3,6-bis{2-[N-(2-methylaminoeth-1-yl)-amido]-1H-indol-6-yl}-9H-carbazole
The title compound was prepared as described in Example 2, using ethyl 6-bromoindolecarboxylate in place of ethyl 5-bromoindolecarboxylate.

Example 21
Preparation of 3,6-bis{2-[N-(2-methylaminoeth-1-yl)-amido]-1H-indol-5-yl}-9-ethyl-carbazole
The title compound was prepared as described in Example 2, using 3,6-dibromo-9-ethyl-carbazole in place of 3,6-dibromocarbazole.

Example 22
Preparation of 5-[3-((2-aminoethyl)carboxamidophenyl) carbazol-6-yl]indole-2-(2-aminoethyl)carboxamide dihydrochloride
Step 1: 3,6-Dibromocarbazole (1.52 g, 4.69 mmol), 1.09 g (4.69 mmol) 2-ethoxycarbonylindole-5-boronic acid, and 5.34 g (35.16 mmol) CsF were dissolved in 50 mL anhydrous dioxane under argon. Pd(OAc)$_2$ (106 mg, 0.47 mmol) and 245 mg (0.70 mmol) dicyclohexylphosphinobiphenyl were dissolved in 20 mL dioxane under argon and added to the above mixture. The resulting mixture was stirred and refluxed under argon overnight, cooled to room temperature, diluted with 200 mL EtOAc and filtered through celite. The filtrate was washed with 3×75 mL $H_2O$. The organic phase was dried over $Na_2SO_4$ and the solvent was evaporated. The residue was purified by flash-column chromatography using hexane/EtOAc (9:1) as eluent.
Step 2: 5-(3-Bromocarbazol-6-yl)indole-2-carboxylic acid ethyl ester (10 mmol), 15 mmol 4-ethoxycarbonylphenyl boronic acid and 45 mmol CsF are dissolved in 100 mL anhydrous dioxane under argon. Pd(OAc)$_2$ (1 mmol) and 1.5 mmol dicyclohexylphosphinobiphenyl are dissolved in 40 mL dioxane under argon and added to the above mixture. The resulting mixture is stirred and refluxed under argon overnight, cooled to room temperature, diluted with 400 mL EtOAc and filtered through celite. The filtrate is washed with 3×150 mL H$_2$O. The organic phase is dried over sodium sulfate and the solvent is evaporated. The residue is purified by flash-column chromatography using a mixture of hexane/EtOAc as eluent.

Step 3: 5-[3-(4-Carboxyethyl-phenyl)carbazol-6-yl]indole-2-carboxylic acid ethyl ester (0.7 mmol) is dissolved in 3.5 mL ethylenediamine in an amber glass vial with a Teflon screw-cap and heated at 55° C. in a sand-bath for 72 h. The excess amine is removed under vacuum and the residue is dissolved in 7 mL DMSO, 0.7 mL TFA is added and the solution is added up to 35 mL by H$_2$O. The solution is purified by preparative HPLC in 7 injections. Appropriate fractions are pooled and evaporated. The residue is dissolved in 7 mL MeOH, divided into 7 centrifuge tubes and cooled in dry ice for 5 min. One mL of 2 N HCl solution in dioxane is added to each tube and the solutions are immediately diluted to 40 mL each by cold Et$_2$O. The suspensions are centrifuged and the supernatant liquids are decanted. The cakes are dissolved in 1 mL MeOH each and precipitated with cold Et$_2$O. The suspensions are centrifuged and the supernatant liquids are decanted. The residues are combined and used in the next step as such.

Example 23

Preparation of 5-[3-((2-guanidinoethyl)carboxamidephenyl) carbazol-6-yl]indole-2-(2-guanidinoethyl)carboxamide 5-[3-((2-Aminoethy)carboxamidephenyl)carbazol-6-yl] indole-2-(2-aminoethyl) carboxamide dihydrochloride, prepared as described in Example 22, (0.5 mmol) is mixed with 2.5 mL DMF, 20 mmol diisopropylethyamine and 10 mmol pyrazole-1-carboxamidine hydrochloride are added and the resulting solution is heated at 55° C. for 24 h. The solvent is removed under vacuum and the residue is dissolved in 5 mL DMSO, 0.5 mL TFA is added and the solution is added up to 25 mL by H$_2$O. The solution is purified by preparative HPLC in 5 injections. Appropriate fractions are pooled and evaporated. The residue is dissolved in 5 mL MeOH, divided into 5 centrifuge tubes and cooled in dry ice for 5 min. One mL of 2 N HCl solution in dioxane is added to each tube and the solutions are immediately diluted to 40 mL each by cold Et$_2$O. The suspensions are centrifuged and the supernatant liquids are decanted. The cakes are dissolved in 1 mL MeOH each and precipitated with cold Et$_2$O. The suspensions are centrifuged and the supernatant liquids are decanted. The residues are dissolved in water and lyophilized.

Biological Examples

Minimum Inhibitory Concentration (MIC) Assays

The assays described below were used to measure the minimum inhibitory concentration (MIC) of a compound necessary to inhibit visible growth of the organism tested. These assays are adapted from NCCLS protocols M7-A4 and M27-A (NCCLS vol 17:9 and vol 17:2) as modified by Sandven, S., *Clin. Micro.* (1999) 37:12, p.3856–3859. MIC values for Aspergillus species were determined using NCCLS protocol M38-P.

Inoculum Preparation, Incubation and Reading Results

All compounds were dissolved in 100% DMSO to a stock concentration of 10 mM and used fresh stock compounds in powder form were kept frozen until needed and used freshly. When used for test purposes, compounds were diluted in the appropriate media depending on the organism being tested.

For yeast and aspergillus species, seven 1:2 serial dilutions of compound in appropriate media buffered with MOPS at pH 7.0 were prepared such that the final starting test compound concentrations were 44.4 $\mu$M for yeast and 50 $\mu$M aspergillus species. For bacteria, dilutions were made in growth media used for the particular bacteria being tested.

Yeast

Five well-separated colonies from a 24 h Sabouraud Dextrose plate incubated at 35° C. were picked and resuspended into 2 mL of normal saline. The O.D.$_{530}$ was read and the culture was adjusted to 0.5 McFarland units with normal saline. A 1:2000 dilution was made with RPMI 1640 media buffered with MOPS at pH 7.0 and 100 $\mu$L of this inoculum preparation was added to an equal volume of test compound-containing media. 25 $\mu$L of the redox indicator Alamar Blue (Biosource International) was added to each well and the plates were incubated for 48 h at 35° C. Wells having yeast growth changed color from blue to pink. Accordingly, the MIC was calculated based on the well with the lowest concentration which did not change color from blue to pink, e.g., growth was inhibited.

Bacteria

Inoculums are made in the same manner as yeast except all dilutions are made in normal saline, with a final dilution of 1:200 and an inoculum of 10 $\mu$L. Solid and liquid media, as well as plate incubation times for the various organisms tested, are listed in the Table below.

| Organism | Liquid Media | Solid Media | 96 Well Plate | Definition |
| --- | --- | --- | --- | --- |
| VRE | BHI | BHIA | No vancomycin- 16 h | BHI-Brain Heart Infusion BHIA-Brain Heart |
| Moraxella catarrhalis | BHI | BHIA | 16 h | Infusion Agar |
| Bacillus cereus | CAMHB | BHIA | 16 h | CAMHB-Cation Adjusted Muller Hinton Broth |
| Pseudemonas aeruginosa | CAMHB | BHIA | 16 h | HTM-Haemophilus Test |
| Staphylococcus aureus | CAMHB | BHIA | 16 h | Media |
| Haemophilus influenzae | HTM | Chocolate Agar | 24 h | Chocolate Agar- Nutrient agar +5% heat lysed sheep blood |

-continued

| Organism | Liquid Media | Solid Media | 96 Well Plate | Definition |
|---|---|---|---|---|
| *Streptococcus pneumoniae* | CAMHB + 5% LHB | MHA + 5% SB | 24 h | LHB-Lysed Horse Blood |
| Aspergillus | RPMI | SABDEX slants | 48 h | SABDEX-SABouraud |
| *Candida species* | RPMI | SABDEX | 48 h | DEXtrose agar MHA-Muller Hinton Agar SB-Sheep Blood |

Filamentous Fungi

Inoculums are made by incubating *Aspergillus species* for 7 days at 35° C. on potato dextrose agar slants. Slants are then covered with 1.0 mL of 0.85% saline, one drop of Tween 20 is added and colonies are teased with a sterile transfer loop to create a suspension which is allowed to sit for 5 min so heavier particles can drop out. The upper suspension is separated and adjusted to an optical density of 0.09 to 0.11. The resulting suspension is diluted 1:50, which yields 2× the final inoculum needed. Micro dilution trays are prepared as with yeast and incubated for 48 h at 35° C. For our purposes the MIC is defined as the lowest compound concentration at which 75% inhibition of growth is observed after 48 h.

Compounds of this invention were tested in assays described above and were found to be active.

DNA Binding Properties of Compounds of this Invention

DNA Thermal Melting Studies

Interactions between DNA and compounds of this invention were investigated using thermal melting techniques. DNA interactions were monitored in a buffer containing 10 mM HEPES, pH 7.2, 0.1 mM EDTA, and 50 mM NaCl. DNA thermal melting was monitored by UV absorbance at 260 nm on a Cary 100 Bio UV/vis spectrophotometer. A 12 base-pair AT-rich DNA oligonucleotide (Oligo 1: CGATTATTAAGC) was used at 5 µM and mixed with compounds at various ratios. Temperature was typically varied from 15 to 95° C. with a ramp rate of 0.2° C./min. To determine the melting temperature (Tm) where half of the double-stranded DNA molecules dissociate into two separated strands, the first-order derivatives of the absorption-temperature curve were calculated using the Varian software, and the maximum of derivatives corresponds to the melting temperature. The melting temperature determined by the derivative methods were verified using a standard hyperchromicity method provided by the Varian software. The Tm value was reported as the difference between melting temperatures in the presence and in the absence of compounds.

Determination of Drug-DNA Binding Constants

An ethidium bromide displacement assay was used to determine the dissociation constant for binding of compounds to oligo 1. The assay was described in Dyatkina et al. *J. Med. Chem.*, 45:805–817, 2002.

Circular Dichroism Studies

Because of the electronic interactions between ligand and DNA, ligand binding can often induce circular dichroism ("CD") signals that are absent when DNA or ligand is alone in solution. DNA binding of compounds of this invention is determined using CD spectroscopy.

What is claimed is:

1. A compound of Formula (I):

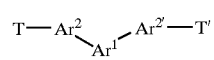

wherein $Ar^1$ is selected from the group consisting of:

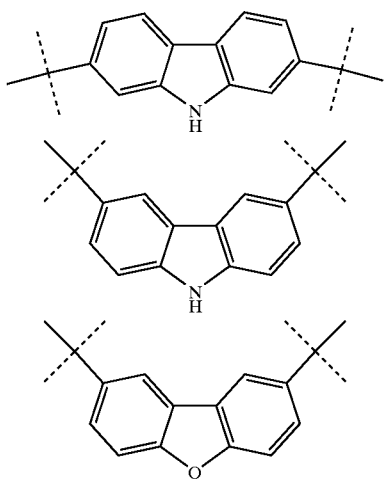

each of $Ar^2$ and $Ar^{2'}$ are independently selected from the group consisting of aryl, substituted aryl, indolyl and substituted indolyl;

T and T' are independently selected from the group consisting of amido, aminoamido, carboxyl, carboxyl ester, amidino, and guanidino;

and further wherein the compounds of Formula I have an MIC of about 50 µM or less when tested for growth inhibition of at least one of the organisms selected from the group consisting of *Candida, Aspergillus, Enterococcus, Staphylococcus, Pseudomonas, Bacillus, Haemophilus, Streptococcus* and *Moraxella*.

2. A compound selected from the group consisting of compounds of Formulae II, and III:

a)

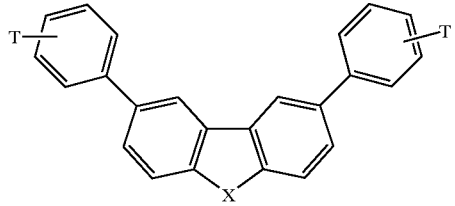

wherein

X=N, or O, and

T is selected from the group consisting of amido, aminoamido, carboxyl, carboxyl ester, amidino and guanidino, and b)

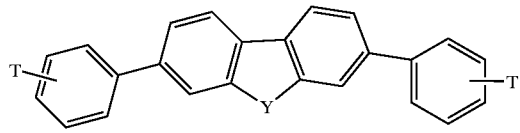

wherein

Y=N, or O, and

T is selected from the group consisting of amido, aminoamido, carboxyl, carboxyl ester, amidino, and guanidino;

with the proviso that the compound is not 2,7-bis{1-[N-(2-aminoeth-1-yl)-amido]phen-3-yl}-9H-carbazole.

3. The compound according to claim 1 wherein $Ar^2$ and $Ar^{2'}$ are independently selected from the group consisting of:

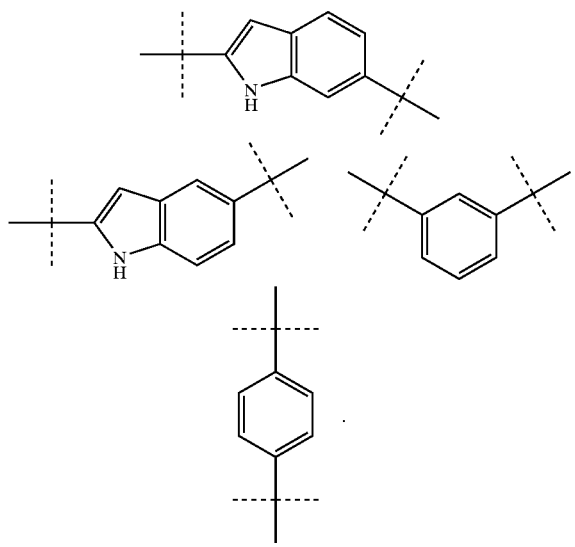

4. The compound according to claim 1 wherein T and T' are independently selected from the group consisting of:

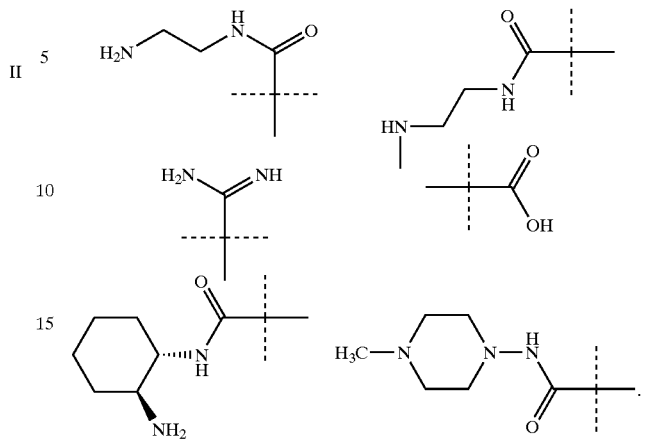

5. A compound selected from the group consisting of:
3,6-bis{2-[N-2-acetamidinoeth-1-yl)amido]1H-indol-5-yl}-9H-carbazole;
3,6-bis{2-[N-(2-aminoeth-1-yl)amido]-1H-indole-5-yl}9H-carbazole;
2,8-bis{1-[N-(2-aminoeth-1-yl)amido]phen-3-yl}dibenzofuran;
2,7-bis{1-[N-(2-aminoeth-1-yl)amido]phen-4-yl}9H-carbazole;
3,6-bis{1-[N-(2-aminoeth-1-yl)amido]phen-3yl}9H-carbazole;
2,8-bis{1-[N-(2-aminoeth-1-yl)amido]phen-4-yl}dibenzofuran;
3,6-bis{2-[N-(2-methylaminoeth-1-yl)amido]-1H-indol-5-yl}-9H-carbazole;
3,6-bis{1-[N-(2-aminoeth-1-yl)amido]phen-4-yl}-9H-carbazole;
3,6-bis[benzamidin-4-yl]-9H-carbazole;
2,7-bis[benzamidin-4-yl]-9H-carbazole;
3,6-bis{2-[N-(2-(morpholin-N-yl)eth-1-yl)amido]-1H-indol-5-yl}-9H-carbazole;
3,6-bis{2-[N-(2-aminocyclohex-1-yl)amido]-1H-indol-5-yl}-9H-carbazole;
3,6-bis{2-[N-(4-methylpiperazin-1-yl)amido]-1H-indol-5-yl}-9H-carbazole;
3,6-bis(1H-indol-5-yl)-9H-carbazole-2',2"-dicarboxylic acid;
2,7-bis{2-[N-(2-methylaminoeth-1-yl)amido]-1H-indol-5-yl}-9H-carbazole;
2,7-bis{2-[N-(2-methylaminoeth-1-yl)amido]-1H-indol-6-yl}-9H-carbazole;
3,6-bis{2-[N-(2-methylaminoeth-1-yl)amido]-1H-indol-6-yl}-9H-carbazole;
3,6-bis{2-[N-(2-guanidinoeth-1-yl)amido]-1H-indol-5-yl}-9H-carbazole;
and pharmaceutically acceptable salts thereof.

6. A pharmaceutical composition comprising a therapeutically effective amount of a compound as defined in claim 1 and a pharmaceutically acceptable carrier.

7. A pharmaceutical composition comprising a therapeutically effective amount of a compound as defined in claim 2 and a pharmaceutically acceptable carrier.

8. A pharmaceutical composition comprising a therapeutically effective amount of a compound as defined in claim 5 and a pharmaceutically acceptable carrier.

* * * * *